United States Patent

Wolfe et al.

[11] 4,391,975
[45] Jul. 5, 1983

[54] PROCESS FOR 1-OXACEPHEM DERIVATIVES

[75] Inventors: Saul Wolfe, Kingston; Chia-Cheng Shaw, Montreal, both of Canada

[73] Assignee: Queen's University at Kingston, Kingston, Canada

[21] Appl. No.: 356,236

[22] Filed: Mar. 8, 1982

Related U.S. Application Data

[63] Continuation-in-part of Ser. No. 330,838, Dec. 15, 1981, abandoned.

[51] Int. Cl.³ .................................................. C07D 498/04
[52] U.S. Cl. ...................................... 544/90; 260/239 A
[58] Field of Search ........................ 544/90; 260/239 A

[56] References Cited

U.S. PATENT DOCUMENTS

| | | | |
|---|---|---|---|
| 4,013,653 | 3/1977 | Wolfe | 544/90 |
| 4,183,855 | 1/1980 | Yoshioka et al. | 544/90 X |
| 4,269,873 | 5/1981 | Christensen et al. | 544/90 X |
| 4,323,567 | 4/1982 | Narisada et al. | 544/90 X |

Primary Examiner—Richard Raymond
Attorney, Agent, or Firm—Richard J. Hicks; Stanley E. Johnson

[57] ABSTRACT

A process for preparing compounds of the formula

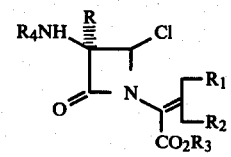

in which

R is hydrogen or methoxy,
$R_1$ is a hydroxyl group,
$R_2$ is chlorine, bromine, OAc or SHET,
$R_3$ is hydrogen or a cleavable carboxy-protecting group preferably selected from loweralkyl, benzyl, benzhydryl, loweralkoxyloweralkyl, loweralkoxybenzyl, phenacyl, trimethylsilyl, 2,2,2-trichloroethyl or pivaloloxy,
$R_4$ is hydrogen or a cleavable amino-protecting acyl group, or $R_4NH$ represents phthalimido, and
HET is a five or six membered aromatic heterocycle containing 1–4 heteroatoms and optionally substituted with loweralkyl, and from which the corresponding 1-oxacephem derivatives can be prepared is described. The novel intermediate compounds of the formula 1 are produced from a penicillin derivative of formula 1 wherein R, $R_3$ and $R_4$ are as above described and $R_1$ and $R_2$ are both the same halogen, by treatment with a formylating agent in a halogenated hydrocarbon solvent to obtain the corresponding compound in which $R_1$ and $R_2$ are both OCHO which is then treated with less than one molar equivalent of a boron halide to obtain a 2:1 to 4:1 mixture of the corresponding compounds of formula 1 in which $R_1$ is OCHO and $R_2$ is the corresponding halogen or $R_1$ is halogen and $R_2$ is OCHO, and in which the former compound predominates. This mixture is separated and the compound in which $R_1$ is OCHO and $R_2$ is halogen is isolated. This last compound is hydrolyzed and the desired intermediate compound in which $R_1$ is OH and $R_2$ is a halogen is isolated. Alternatively, the compound of formula 1 in which $R_1$ is OCHO and $R_2$ is halogen is subjected to displacement by −OAc or HSHET prior to the hydrolysis.

13 Claims, No Drawings

PROCESS FOR 1-OXACEPHEM DERIVATIVES

RELATION TO OTHER APPLICATIONS

This application is a continuation-in-part of our earlier U.S. application Ser. No. 330,838 filed Dec. 15, 1981, now abandoned.

BACKGROUND OF THE INVENTION (a) Field of Invention

This invention relates to sulfur-free penicillin derivatives and more particularly to derivatives of 2-azetidinyl-3-methyl-2-butenoates having two different functions at the 3-methyl and at the terminal methyl groups of the 2-butenoate chain and to a process for preparing said derivatives. The derivatives of the present invention are particularly useful as intermediates in the synthesis of 1-oxacephems having substituents other than methyl and hydroxyl attached to carbon-3 of the six membered ring. 1-Oxacephems are cephalosporin analogs in which the sulfur atom of the six membered ring has been replaced by oxygen. The 1-oxacephems have been found to possess anti-bacterial activity in any of their free acid, salt or active ester forms.

(b) Prior Art

Numerous routes for the synthesis of the 1-oxacephem ring system have been described in the literature and these are believed to be the most relevant prior art relating to the present invention. In addition, at least six different methods exist for the replacement of R=H of structures 1, A, B, C, D and the corresponding hydrogen of penicillins, cephalosporins and oxacephems by R=OCH$_3$ (Topics in Antibiotic Chemistry, Vol. 4, Edited by P. Sammes, pp 196–210).

The first publications on 1-oxacephems appeared simultaneously in the Canadian Journal of Chemistry, Volume 52, page 3996 (1974) by S. Wolfe et al., and in the Journal of the American Chemical Society, Volume 96, page 7582 (1974) by B. G. Christensen et al., and illustrate the two main lines followed subsequently by other workers.

In the approach employed by S. Wolfe et al, the starting material was penicillin, which was converted to a 2-azetidinyl-3-methyl-2-butenoate.

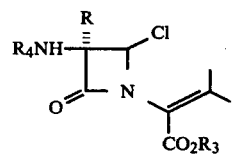

A

The isoprenoid skeleton attached to the nitrogen atom of the azetidinyl moiety was retained during the remainder of the sequence, which was therefore directed towards a Z-2-azetidinyl-4-hydroxy-3-methyl-2-butenoate, e.g., 1, R$_2$=H, which was finally cyclized to form the 1-oxacephem (see also Canadian Pat. No. 1,052,787 issued Apr. 17, 1979 to Wolfe). Variations of this approach have been described by C. U. Kim and D. N. McGregor, Tetrahedron Letters, page 409 (1978), Y. Hamashima et al., Tetrahedron Letters, page 4943 (1979), J. E. Baldwin et al., Tetrahedron, Volume 36, page 1627 (1980), and J. L. Pfeil et al, Journal of Organic Chemistry, Volume 46, page 827 (1981). A review of several approaches, including this one, to the antibacterial agent "Moxalactam" ® is given by W. Nagata, Philosophical Transactions of the Royal Society, Part B, Volume 289, page 225 (1980).

In the approach used by B. G. Christensen et al., a phosphorus-containing compound such as B or C was subjected to an intramolecular Wittig cyclization to form the six-membered ring. Compounds such as B or C (below) may be prepared by total synthesis, as in the work of B. G. Christensen et al., or by partial synthesis from a penicillin or cephalosporin precursor. In the latter case, as described by R. B. Woodward et al., Nouveau Journal de Chimie, Volume 1, page 85 (1977), and first disclosed by K. Heusler in Cephalosporins and Penicillins, Chemistry and Biology, Edited by E. H. Flynn, Academic Press, New York, 1972, page 274, the isoprenoid moiety is detached from the azetidinyl nitrogen atom of a compound such as A, and the required phosphorane or phosphonate is constructed by successive reactions with a glyoxylate ester, thionyl chloride, and a phosphorous compound. Examples of the latter approach have been reviewed, inter alia, by E. T. Gunda and J. Cs. Jaszberenyi, Progress in Medicinal Chemistry, Edited by G. P. Ellis and G. B. West, Elsevier/North Holland Biomedical Press, Volume 12, Chapter 8 and Volume 14, Chapter 4, 1975 and 1977; also in Topics in Antibiotic Chemistry, Edited by P. G. Sammes, Volume 4, Ellis Horwood Limited, 1980, Chapters 2 and 3. According to Nagata (op cit), this multi-step approach necessitates the repetitive steps of removing and supplying several carbon atoms, and results in a very low overall yield of the final product.

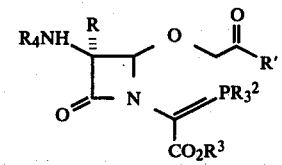

B

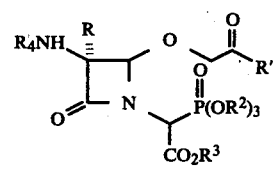

C

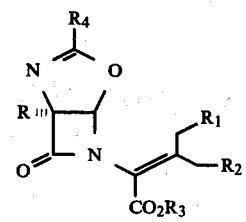

D

In the work of Yamashima et al. (op cit) and M. M. Campbell et al., Tetrahedron Letters, page 1257 (1979), compounds of type D, which contain a 2-azetidinyl-3- and 4-functionalized-2-butenoate (R$^1$=OCHO, R$^2$=OCHO, OAc) were found to be unsuitable for the preparation of 1-oxacephem compounds, because of problems associated with the removal of the R$^1$ protecting group in the presence of an oxazoline ring.

Although some of the processes disclosed in the Prior Art use functionalized derivatives of 2-azetidinyl-3-methyl-2-butenoates as intermediates, none of those processes has succeeded so far in preparing such intermediates having two different functions at the 3-methyl and at the terminal methyl groups of the 2-butenoate chain. Such intermediates would be particularly valuable for the preparation of 1-oxacephem antibiotics having a methylthioheterocyclyl substituent in position 3 of the 1-oxacephem ring system, because they would enable the chemist to introduce such a substituent in a particularly facile manner.

(c) Objects of the Invention

An object of the present invention is to provide intermediates of the general formula:

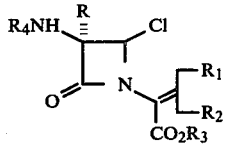

in which:
R is hydrogen or methoxy,
$R_1$ is a hydroxyl group,
$R_2$ is chlorine, bromine, OAc or SHET,
$R_3$ is hydrogen or a cleavable carboxy-protecting group preferably selected from loweralkyl, benzyl, benzhydryl, lower-alkoxyloweralkyl, loweralkoxybenzyl, phenacyl, trimethylsilyl, 2,2,2-trichloroethyl or pivaloyloxy,
$R_4$ is hydrogen or a cleavable amino-protecting acyl group, or $R_4NH$ represents phthalimido, and
HET is a five or six membered aromatic heterocycle containing 1-4 heteroatoms and optionally substituted with loweralkyl.

Another object of the present invention is to provide a simple and efficient process for the production of the intermediate Compound 1 from a 2-azetidinyl-3-methyl-2-butenoate.

Yet another object of the present invention is to provide a process for the cyclization of the intermediate compounds 1 to 1-oxacephems of the general formula

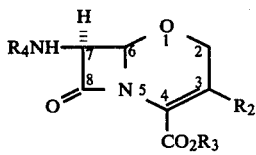

where $R_3$ is as heretobefore described, $R_4$ is hydrogen, and $R_2$ is a substituted methyl not a methyl group, which compounds are readily convertible to a range of compounds of the general formula

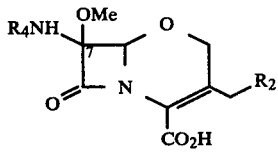

where $R_2$ and $R_4$ are as hereinbefore described, and the methoxyl group at C(7) has been introduced by one of the procedures noted in the Prior Art.

These intermediates are readily convertible to known oxacephem anti-bacterial agents such as Moxalactam ® by known methods. For example the compound of formula 1 in which R is hydrogen, $R_1$ is hydroxy, $R_2$ is SHET in which HET is 1-methyl-1H-tetrazol-5-yl, $R_3$ is a cleavable carboxy-protecting group, e.g. diphenylmethyl, and $R_4$ is a cleavable amino-protecting group, e.g. trichloroethoxycarbonyl, may be treated with t-butyldiphenylchlorosilane to obtain the corresponding t-butyldiphenylsilyl derivative which is then cyclized by treatment with fluoride ions to yield the corresponding 1-oxacephem derivative of formula I

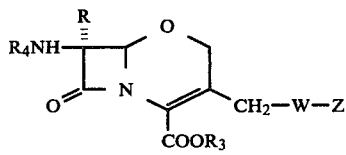

in which R is hydrogen, $R_3$ and $R_4$ are as defined above, W is sulfur, and Z is 1-methyl-1H-tetrazol-5-yl; treatment of said last-named compound with activated zinc yields the corresponding free 7β-amino compound which is identical with compound (II) described in Drugs of the Future, Vol. IV, No. 9, 667–671 (1979) which also shows the conversion of the latter compound to Moxalactam ®. Alternatively, the compound of formula I in which R, $R_3$, $R_4$, W and Z are as defined above may be treated with t-butylhypochlorite and lithium methoxide in the manner described by Nagata (op.sit) to obtain the corresponding compound of formula I in which R is methoxy, $R_3$, $R_4$, W and Z are as defined above, and which is identical with compound 32 of Chart 6 of the above reference; the conversion of the latter compound to Moxalactam ® is then described in Chart 7 of said reference. Other pathways will be apparent to those skilled in the art.

The term "acyl" as used herein includes 2,2,2-trichloroethoxycarbonyl, phenoxycarbonyl and in general alkoxycarbonyl or aryloxycarbonyl, alkyl or arylcarbamoyl and the like, since such compounds do not undergo intramolecular displacement of chlorine by acyl under the conditions of cyclization to the oxacephem ring system.

Carboxy or protected carboxy groups conventional in the chemistry of penicillins and cephalosporins, usually contain up to 20 carbon atoms and are preferably selected from loweralkyl, benzyl, benzhydryl, loweralkoxyloweralkyl, loweralkoxybenzyl, phenacyl, trimethylsilyl, 2,2,2-trichloroethyl or pivaloyloxy. The protective groups can be the same or different for each carboxyl in the molecule. The structures of the carboxy protecting groups can vary widely without changing the import of this invention. Usually the protective groups are removed to give free carboxy or salts, at any stage of synthesis. Therefore, the structures of the carboxy-protective groups can vary widely without changing the gist of this invention. In other words, their structures have no specific significance other than protection, deprotection, and, when included, salt formation.

Specific examples of said protective groups are esters (including optionally substituted 1-5C esters, e.g. methyl, ethyl, isopropyl, n-butyl, t-butyl, pentyl, cyclopropylmethyl, monohydroxy-t-butyl, 2,2,2-trichloroethyl, chloromethyl, cyanomethyl, methanosulfonylethyl, acetylmethyl, acetoxymethyl, propionyloxymethyl, benzoyloxymethyl, methoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, and allyl esters; aralkyl esters e.g. benzyl, phenethyl, tolylmethyl, dimethylbenzyl, nitrobenzyl, halobenzyl, methoxybenzyl, phthalidyl, p-hydroxy-di-t-butylbenzyl, diphenylmethyl, trityl, phenacyl, chlorophenacyl, bromophenacyl, nitrophenacyl, and methylphenacyl esters; and other easily removable aliphatic esters; metal esters, e.g. trimethylsilyl, dimethylmethoxysilyl, trimethylstannyl esters; and aromatic esters, e.g. phenyl, naphthyl, tolyl, dimethylphenyl, nitrophenyl, methanosulfonylphenyl, chlorophenyl, pentachlorophenyl, indenyl, and pyridyl esters); or pharmaceutically acceptable salts (including alkali metal salts, e.g. sodium and potassium salts; alkaline earth metal salts, e.g. magnesium, calcium and acyloxycalcium salts; and salts with organic bases, e.g. procaine, triethylamine and dicyclohexylamine). Each carboxy in the molecule can be free or protected by the same or different groups.

The heterocyclic ring HET in SHET is a 5 or 6 membered ring and has 1 to 4, preferably 1-3 heteroatoms which are the same or different and contain oxygen, sulphur or nitrogen. An unsaturated heterocyclic ring containing 2 double bonds is preferred. The heterocyclic ring can have one or several, preferably 1 or 2, substitutions therein. The substituent can be selected from: halogen, such as fluorine, chlorine, bromine and iodine and preferably chlorine and bromine, amino, lower alkylamino, di-lower alkylamino, lower alkyl, cycloalkyl (with 3 to 7, preferably 5 or 6 carbon atoms in cycloalkyl), lower alkyloxy, trifluoromethyl, phenyl, benzyl, and acylamino with preferably 2-5 and even more preferred 2 or 3 carbon atoms. Examples of preferred HET include furyl, thienyl,

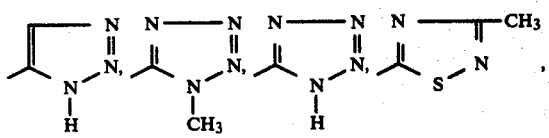

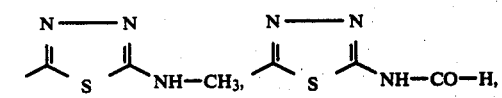

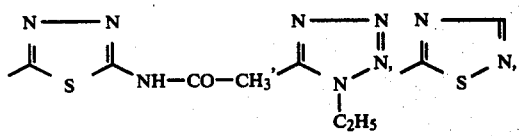

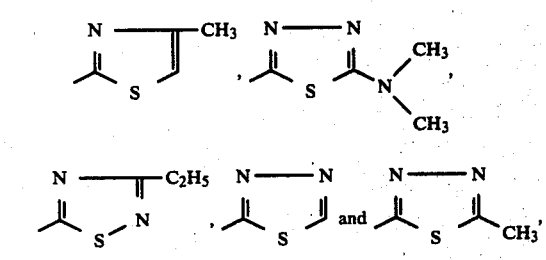

Illustrative of the compounds 1 of the present invention

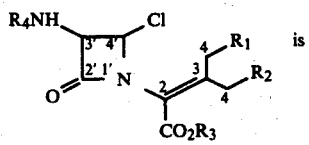 is

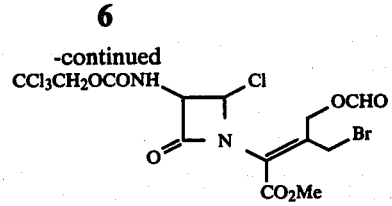

which is methyl 2-(2'-oxo-3'S-trichloroethoxycarbonylamino-4'-chloro) azetidinyl-3-bromomethyl-4-formyloxy-trans-2-butenoate.

Other examples include:

| $R_3$ | $R_2$ | $R_1$ | $R_4$ |
|---|---|---|---|
| $CH_2CCl_3$ or $CH_3$ | Cl | OCHO | $CCl_3CH_2OCO$ |
| " | OAc | " | " |
| " | S Het | " | " |
| " | Br | OH | " |
| " | Cl | " | " |
| " | OAc | " | " |
| " | S Het | " | " |
| " | Br | " | PhOCO |
| " | Cl | " | " |
| " | OAc | " | " |
| " | S Het | " | " |
| " | Br | OCHO | " |
| " | Cl | " | " |
| " | OAc | " | " |
| " | S Het | " | " |

| $R_3$ | $R_2$ | $R_1$ | $R_4NH$ |
|---|---|---|---|
| $CH_2CCl_3$ or $CH_3$ | Br | OCHO | Phthalimido |
| " | Cl | " | " |
| " | OAc | " | " |
| " | S Het | " | " |
| " | Br | OH | " |
| " | Cl | " | " |
| " | OAc | " | " |
| " | S Het | " | " |

BRIEF DESCRIPTION OF INVENTION

Thus, by one aspect of the invention there is provided a process for preparing a 1-oxacephem derivative of the formula I

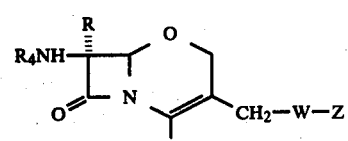

in which $R_4$ is hydrogen or a cleavable amino-protecting acyl group, or $R_4NH$ represents phthalimido, $R_3$ is hydrogen or a cleavable carboxy-protecting group, R is hydrogen or methoxy, W is NH, O, or S, and Z is selected from lower acyl groups and from five membered heterocycles containing 1-4 heteroatoms and optionally substituted with loweralkyl as defined hereinbefore characterized by treating a compound of the formula II

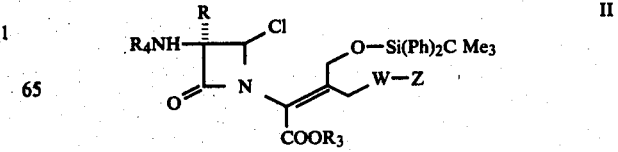

in which $R_4$, $R_3$, R, W, and Z are as defined above, with fluoride ions, and isolating the corresponding compound of formula I.

By another aspect of the invention there is provided a process for treating a compound of the formula III

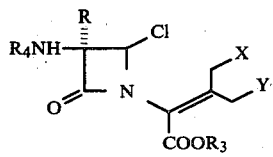

in which $R_4$, $R_3$ and R are as defined above, and X and Y are the same halogen, (a) with a formylating agent in a halogenated hydrocarbon solvent to obtain the corresponding compound of formula III in which X and Y are both OCHO;

(b) treating said last-named compound with less than one molar equivalent of a boron halide, to obtain a 2:1 to 4:1 mixture of the compounds of formula III in which X is OCHO and Y is the halogen derived from the boron halide or in which X is the halogen derived from the boron halide and Y is OCHO; separating said last-named mixture and isolating the corresponding major proportion compound of formula III in which X is OCHO and Y is the desired halogen;

(c) treating said last-named compound of formula III in which X is OCHO and Y is the halogen with a hydrolyzing agent and isolating the compound of formula III in which X is OH and Y is the halogen;

(d) alternatively, treating the last-named compound of formula III of (b) with a tetraalkylammonium acetate or with a heterocyclic mercaptan of the general formula HSHET, where HET is as hereinabove described, and isolating the corresponding product of formula III in which X is OCHO and Y is OAc or SHET prior to the hydrolysis step of (c).

By yet another aspect there is provided 2-azetidinyl-3-methyl-2-butenoates of the formula

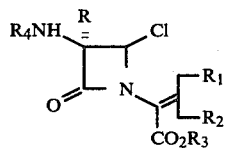

in which

R is hydrogen or methoxy, $R_1$ is a hydroxyl group, $R_2$ is chlorine, bromine, OAc or SHET, $R_3$ is hydrogen or a cleavable carboxy-protecting group preferably selected from loweralkyl, benzyl, benzhydryl, loweralkoxyloweralkyl, loweralkoxy-benzyl, phenacyl, trimethylsilyl, 2,2,2-trichloroethyl or pivaloyloxy, $R_4$ is hydrogen or a cleavable amino-protecting acyl group, or $R_4NH$ represents phthalimido, and HET is a five or six membered aromatic heterocycle containing 1-4 hetero atoms and optionally substituted with loweralkyl. Typical examples of HET include furyl, thienyl,

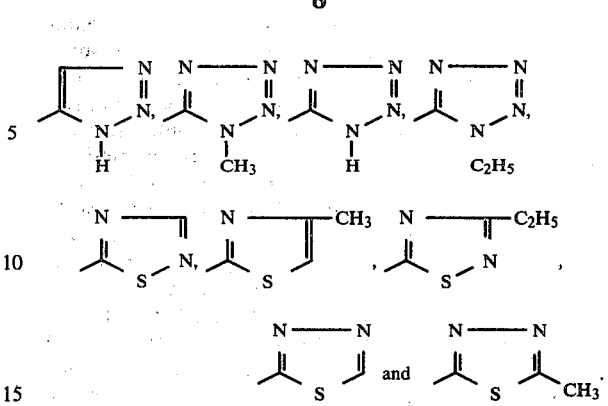

DETAILED DESCRIPTION OF PREFERRED EMBODIMENTS

This invention is particularly concerned with the elaboration of routes to compounds of type 1, in which $R_1=OH$ and $R_2 \neq H$, by functionalization of a 2-azetidinylbutenoate. Important intermediates in these sequences are the diformates IV A, V A and VI A which are prepared from the dibromo precursors IV B, V B and VI B.

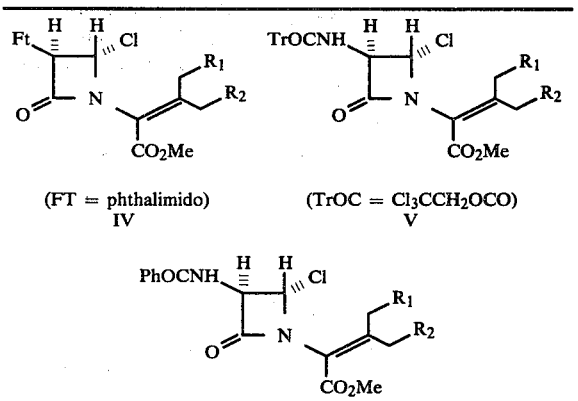

(FT = phthalimido)  (TrOC = $Cl_3CCH_2OCO$)
IV                   V (PhOC = PhOCO)
VI

| A: $R_1 = R_2 =$ OCHO | J: $R_1 =$ OH; $R_2 =$ Br |
|---|---|
| B: $R_1 = R_2 =$ Br | K: $R_1 =$ OTHP; $R_2 =$ Br |
| C: $R_1 =$ Br; $R_2 =$ H | L: $R_1 =$ Ot-Butyldimethylsilyl; $R_2 =$ Br |
| D: $R_1 =$ H; $R_2 =$ Br | M: $R_1 =$ OCHO; $R_2 =$ Cl |
| E: $R_1 =$ H; $R_2 =$ OCHO | N: $R_1 =$ Cl; $R_2 =$ OCHO |
| F: $R_1 =$ OCHO: $R_2 =$ H | O: $R_1 =$ OH: $R_2 =$ Cl |
| G: $R_1 = R_2 =$ Cl | P: $R_1 =$ OAc; $R_2 =$ OCHO |
| H: $R_1 =$ OCHO; $R_2 =$ Br | Q: $R_1 =$ OCHO; $R_2 =$ OAc |
| I: $R_1 =$ Br; $R_2 =$ OCHO | R: $R_1 =$ OH; $R_2 =$ OAc |

In an earlier investigation of the displacement of bromine from IV C and IV D (S. Wolfe et al., Can. Journal Chem. 50, 2898 (1972)), it was observed that a 1:1 mixture of these monobromides is converted in over 90% isolated yield to a 2:1 mixture of E (IV E) and Z (IV F) formates, using tetramethylguanidinium formate in chloroform solvent at room temperature. Under the same conditions, IV A was not obtained from the dibromide IV B. It has now been found that simply changing the solvent from chloroform to methylene chloride allows the isolation of IV A in 21-28% yield, using tetramethylguanidinium formate at −10° C., and in 42-47% yield using tetra-n-butylammonium formate at room temperature. Similar conditions are employed to prepare V A and VI A.

Although it appears reasonable to suppose that the conversion of a dibromide to a diformate would proceed via a mixture of the bromoformates VII and VIII at an intermediate stage, such compounds have not been isolated from any of the reactions of IV B, V B and VI B. These multiply functionalized butenoates are, however, accessible from the reactions of the diformates with boron halides.

Experiments with the phthalimido compound IV A reveal that one mol-equiv of boron tribromide regenerates the dibromide IV B in quantitative yield; use of boron trichloride leads to the dichloride IV G. With 0.6 mol-equiv of boron tribromide, IV A is converted in 75% yield to a 2:1 mixture of the bromoformates IV H and IV I, from which the major isomer IV H, m.p. 135°–137° C., can be isolated in pure form. The assignment of the E configuration to this compound is based on the finding that deformylation under acidic conditions ($HCl$—$MeOH$—$CH_2Cl_2$) leads to the bromohydrin IV J, convertible to the tetrahydropyranyl ether IV K and the t-butyldimethylsilyl ether IV L. Under the same deformylation conditions the minor isomer IV I is converted to the bromolactone IX ($R_4NH=Ft$; $R_1=Br$), and the diformate IV A affords the hydroxylactone IX ($R_4NH=Ft$; $R_1=OH$). The hydroxylacetone is convertible to the bromolactone upon further treatment with boron tribromide. The tetrahydropyranyl and t-butyldimethylsilyl derivatives of this compound can also be prepared.

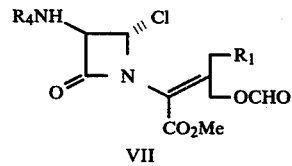

VII

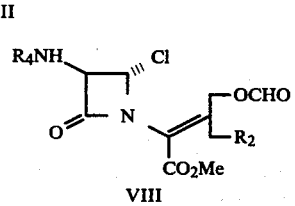

VIII

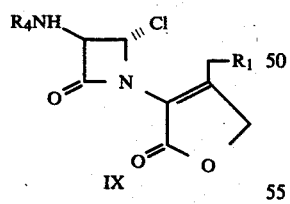

IX

With 0.6 mol-equiv of boron trichloride, IV A gives, in 68% yield, a 3:1 mixture of the isomeric chloroformates IV M and IV N, the assignment of configuration again being based on the deformylation of IV M to the chlorohydrin IV O, and of IV N to the chlorolactone IX ($R_4NH=Ft$; $R_1=Cl$).

The sequences just described are also compatible with the TrOC (V A) and PhOC (VI A) side chains. Deformylation of V A and VI A leads to IX ($R_4=TrOC$; $R_1=OH$) (quantitative) and IX ($R=PhOC$; $R_1=OH$) (91%), respectively. Boron tribromide affords a separable 4:1 mixture of V H and V I (61%) from V A, and a 4:1 mixture of VI H and VI I (61%) from VI A.

Thus, in the replacement of formate by halogen, as in the earlier replacement of halogen by formate (S. Wolfe et al., Can.Journal Chem. 50, 2898 (1972)), the E-geometrical isomer (IV H, IV M, V H, VI H) is formed preferentially. However, despite their stereochemical similarities, the two reactions appear to proceed via different mechanisms. Indeed, that as many as three different pathways may exist for the displacement of one allylic substituent by another in such compounds becomes apparent when the bromo-formates IV H, V H and V I are allowed to react with tetraethylammonium acetate, to form acetoxyformates.

In the phthalimido series, this reaction proceeds with inversion of olefinic geometry to yield IV P (60%), with no trace of the geometrical isomer IV Q. On the other hand, both TrOC compounds undergo displacement by acetate with retention of olefinic geometry. Thus, V H affords V Q, and V I affords V P. In each case, the configurations of the acetoxyformates are established by deformylation experiments: IV P and V P are converted to the acetoxylactones IX ($R_4NH=Ft$, TrOCNH; $R_1=OAc$), but V Q gives the acetoxyhydrin V R.

The bromoformate V H is also converted to the mercaptomethyltetrazole derivative X, with mercaptomethyltetrazole in dimethylformamide solvent. Deformylation affords the alcohol of type XI, which corresponds to 1.

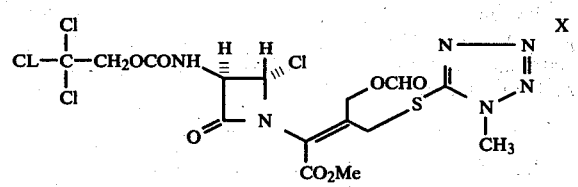

X

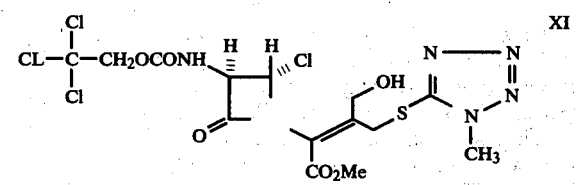

XI

EXAMPLE 1

Preparation of diformate IV A

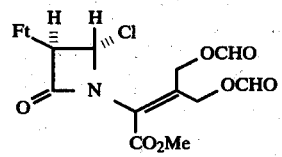

To a solution of IV B (2.35 g, 4.52 mmol), in methylene chloride (5 mL), was added, during 30 min, a solution of tetra-n-butylammonium formate (3.73 g, 13.56 mmol) in methylene chloride (20 mL). The reaction mixture was stirred for 48 h under nitrogen at room temperature and was then diluted with 10% acetone-hexane (10 mL) and chromatographed on silica gel. Graded elution with acetone-hexane afforded 919 mg (45%) of the diformate IV A as a pale yellow foam. $^1$Hmr (CDCl$_3$, δ): 3.87 (3H, s), 5.00 (2H, s), 5.23 (2H, s), 5.57 (1H, d, 2 Hz), 6.23 (1H, d, 2 Hz), 7.73 (4H, d), 7.97 (2H, s); ir (CHCl$_3$): 1795, 1775, 1735 cm$^{-1}$. Anal. calcd. for C$_{19}$H$_{15}$N$_2$O$_9$Cl: C, 50.62; H, 3.35; N, 6.22 Found: C, 50.37; H, 3.46; N, 6.18.

EXAMPLE 2

Hydrolysis of diformate IV A to Hydroxylactone IX (R$_4$NH=Ft, R$_1$=OH)

The diformate IV A (102 mg, 0.226 mmol) was dissolved in methylene chloride (4 mL), and N methanolic hydrogen chloride (0.2 mL) was added. The reaction mixture was stirred at 25° C. for 2 h, and the solvent was then removed. The residue (89 mg) was a pale yellow foam, which appeared homogeneous on tlc. It was purified by plc (silica gel, acetone:hexane, 2:3) to give 79 mg (96%) of IX (R$_4$NH=Ft; R$_1$=OH); ir (CHCl$_3$): 1790, 1770, 1725 cm$^{-1}$; $^1$Hmr (CDCl$_3$, δ): 3.00 (1H, br s, exch D$_2$O), 4.54 4.81 (2H, ABq, J=16 Hz), 4.95 (2H, s), 5.53 (1H, d, 2 Hz), 6.57 (1H, d, 2 Hz) 7.68 (4H, br s).

EXAMPLE 3

Conversion of IV A to IV B with Excess Boron Tribromide

To an ice-cold solution of the diformate IV A (52 mg, 0.115 mmol), in methylene chloride (3 mL), was added an ice-cold solution of boron tribromide (30 mg, 0.116 mmol) in methylene chloride (0.25 mL). The solution was stirred at 0° C. for 1.5 h and then poured onto ice-cold brine (20 mL) and the layers separated. The aqueous layer was extracted with chloroform (3×40 mL) and the combined organic layers were washed with brine (2×5 mL), dried (MgSO$_4$) and evaporated to give 59 mg (100%) of IV B as a colourless foam. The $^1$Hmr spectrum of the product was identical with that of authentic material.

EXAMPLE 4

Reaction of IV A with 0.5 Mol-Equiv of Boron Tribromide

To an ice-cold solution of the diformate (304 mg, 0.675 mmol), in methylene chloride (5 mL), was added dropwise, with stirring, a solution of boron tribromide (86 mg, 0.34 mmol) in methylene chloride (0.8 mL). Stirring was continued for 1.5 h at 0° C., and the solution was then poured onto ice-cold 5% sodium bicarbonate. The layers were separated and the aqueous layer was extracted with methylene chloride (3×60 mL). The combined organic layers were washed with brine (3×10 mL), dried (Na$_2$SO$_4$) and evaporated to a colourless foam (322 mg). This was purified by plc (silica gel, acetone:hexane, 1:4) to give three products. The leading band was IV B (25 mg). The middle band was a 79/21 mixture of IV H and IV I (245 mg, 75%). Separation and characterization of these two compounds is described in the following example.

EXAMPLE 5

Preparation of IV H and IV I

To an ice-cold solution of IV A (937 mg, 2.08 mmol), in methylene chloride (10 mL), was added, dropwise under a nitrogen atmosphere, a solution of boron tribromide (321 mg, 1.28 mmol, 0.61 mol-equiv) in methylene chloride (6 mL). The mixture was stirred for 1.5 h at 0° C. and then poured into a large excess of saturated ice-cold sodium bicarbonate. Isolation as described above afforded a crude product which was chromatographed on silica gel. Elution with 1% acetone in hexane afforded successively the dibromide IV B (trace), IV H (343 mg, 34%), IV I (176 mg, 17%), unreacted IV A (trace), and an unidentified compound. IV H: m.p. 135.0°–137.0° C.; ir (CHCl$_3$): 1800, 1780, 1730 cm$^{-1}$; $^1$Hmr (CDCl$_3$, δ): 4.00 (3H, s), 4.59, 4.86 (2H, ABq, 10 Hz), 5.17 (2H, s), 5.67 (1H, d, 2 Hz), 6.35 (1H, d, 2 Hz), 7.90 (4H, br s), 8.17 (1H, s). Anal. calcd. for C$_{18}$H$_{14}$N$_2$O$_7$BrCl: C, 44.51; H, 2.91; N, 5.77; Br, 16.45; Cl, 7.30. Found: C, 44.37; H, 3.02; N, 5.74; Br, 16.47; Cl, 7.47.

IV I: foam; $^1$Hmr (CDCl$_3$, δ), 4.05 (3H, 2), 4.47, 4.64 (2H, ABq, 10 Hz), 5.53 (2H, s), 5.76 (1H, d, 2 Hz), 6.47 (1H, d, 2 Hz), 8.03 (4H, br s), 8.27 (1H, 2).

EXAMPLE 6

Conversion of IV A to IV G, IV M and IV N with Boron Trichloride

To an ice-cold solution of IV A (131 mg, 0.29 mmol) in methylene chloride (4 mL) was added 0.2 mL of a M solution of boron trichloride in methylene chloride (0.07 mol-equiv). The resulting solution was stirred for 2 h at 0° C. and then poured into ice-cold 5% sodium bicarbonate. The aqueous layer was extracted with methylene chloride (3×50 mL), and the combined organic extracts were washed with brine (2×20 mL), dried (Na$_2$SO$_4$) and evaporated to 133 mg of a foam. This was purified by plc (silica gel, 30% acetone in hexane) to give three products: the dichloride IV G (8 mg, 6%); $^1$Hmr (CDCl$_3$, δ): 3.93 (3H, s), 4.47, 4.62 (2H, ABq, 12 Hz), 4.71, 4.89 (2H, ABq, 12 Hz), 5.65 (1H, d, 2 Hz), 6.25 (1H, d, 2 Hz), 7.83 (4H, d); and a 3:1 mixture of IV M and IV N (84 mg, 68%). IV M: $^1$Hmr (CDCl$_3$, δ): 3.93 (3H, s), 4.66, 4.78 (2H, ABq, 12 Hz), 5.07 (2H, br s), 5.61 (1H, d, 2 Hz), 6.27 (1H, d, 2 Hz), 7.80 (4H, d), 8.10 (1H, s).

IV N: $^1$Hmr (CDCl$_3$, δ): 3.91 (3H, s), 4.36, 4.53 (2H, ABq, 11 Hz), 5.37 (2H, s), 5.61 (1H, d, 2 Hz), 6.27 (1H, d, 2 Hz), 7.80 (4H, d), 8.10 (1H, s).

EXAMPLE 7

Hydrolysis of IV H to the Bromohydrin IV J

The bromoformate IV H (87 mg, 0.18 mmol), in methylene chloride (4 mL), was cooled to 0° C. and 0.2 mL of 3.2 M methanolic hydrogen bromide was added. The resulting solution was stored at 0° for 1.5 h and then poured onto ice-cold 2.5% potassium bicarbonate (20 mL). The aqueous phase was extracted with methylene chloride (3×50 mL), and the combined organic layers were then washed with brine (2×20 mL), water (2×20 mL), dried (Na$_2$SO$_4$) and evaporated. The crude product, 73 mg of a nearly colourless foam, was purified by plc on silica gel buffered at pH 7.65 with boric acid-borax. Five developments with 20% acetone in hexane yielded 45 mg of IV J. $^1$Hmr (CDCl$_3$, δ): 2.87 (1H, br s, exch D$_2$O), 3.92 (3H, s), 4.43 (2H, s), 4.55, 4.72 (2H, ABq, 10 Hz), 5.60 (1H, d, 1.8 Hz), 6.27 (1H, d, 1.8 Hz), 7.83 (4H, d).

EXAMPLE 8

Hydrolysis of IV M to the Chlorohydrin IV O

The chloroformate IV M (53 mg, 0.12 mmol), in methylene chloride (3 mL), was cooled to 0° C. and 0.15 mL of N methanolic hydrogen chloride was added. The resulting solution was stored for 2 h at 0° C., and then worked up as described above for IV J to give the chlorohydrin IV O, 49 mg, $^1$Hmr (CDCl$_3$, δ): 2.87 (1H, br s, exch D$_2$O), 3.90 (3H, s), 4.41 (2H, s), 4.62, 4.76 (2H, ABq, 12 Hz), 5.60 (1H, d, 1.8 Hz), 6.23 (1H, d, 1.8 Hz), 7.77 (4H, s).

EXAMPLE 9

Hydrolysis of IV I to the Bromolactone IX (R$_4$NH=Ft; R$_1$=Br)

The bromoformate IV I (59 mg, 0.122 mmol), in methylene chloride (3 mL), was cooled to 0° C. and 0.15 mL of 3.2 M methanolic hydrogen chloride was added. The resulting solution was stored at 0° C. for 1.5 h, and the product was then isolated as described above; 35 mg, $^1$Hmr (CDCl$_3$, δ): 4.41, 4.72 (2H, Abq, 12 Hz), 5.00 (2H, s), 5.67 (1H, d, 2 Hz), 6.70 (1H, d, 2 Hz), 7.87 (4H, d).

EXAMPLE 10

Conversion of IX (R$_4$NH=Ft; R$_1$=OH) to IX (R$_4$NH=Ft; R$_1$=Br)

The hydroxylactone, prepared by deformylation of IV (92 mg, 0.2 mmol), was dissolved in methylene chloride (3.5 mL) and, at 0° C., boron tribromide (0.1 mL) was added. The resulting solution was stirred at 0° C. for 48 h and the product was then isolated in the usual manner to yield 80 mg (94% from IV A) of the bromolactone, identical to the material described above.

EXAMPLE 11

Tetrahydropyranylation of IX (R$_4$NH=Ft; R$_1$=OH)

The hydroxylactone (86 mg) (prepared from 104 mg, 0.23 mmol of IV A) was dissolved in dry tetrahydrofuran (5 mL). To this solution were added freshly purified dihydropyran (0.5 mL) and boron trifluoride etherate (0.2 mL). The resulting solution was stirred for 2 h at room temperature and was then poured into ice-cold 5% sodium bicarbonate (20 mL). The mixture was extracted with chloroform (3×40 mL), and the combined organic extracts were washed with brine (2×20 mL), dried (Na$_2$SO$_4$) and evaporated to give the crude product as an oil. This was purified by plc (silica gel, acetone:hexane, 2:3) to yield the tetrahydropyranyl ether IX (R$_4$NH=Ft; R$_1$=OTHP), 97 mg (94% from IV A). $^1$Hmr (CDCl$_3$, δ): 1.65 (6H, m), 3.67 (2H, m), 4.59, 4.79 (2H, br ABq, 12 Hz), 4.83 (1H, br, s), 5.00 (2H, br s), 5.60 (1H, d, 2 Hz), 6.67 (1H, d, 2 Hz), 7.80 (4H, d).

EXAMPLE 12

Silylation of IX (R$_4$NH=Ft; R$_1$=OH)

The hydroxylactone (72 mg), prepared from IV A (86 mg, 0.19 mmol), was dissolved in dimethylformamide (2.5 mL), and the solution was treated successively with imidazole (30 mg, 0.44 mmol) and t-butyldimethylchlorosilane (30 mg, 0.2 mmol). The reaction mixture was stirred for 1 h at room temperature, and the solvent was then removed under reduced pressure at 40°-45° C. The residue was purified by plc (silica gel, 20% acetone in hexane) to yield 60 mg (65% from IV A) of the t-butyldimethylsilyl ether. $^1$Hmr (CDCl$_3$, δ): 0.13 (6H, s), 0.92 (9H, s), 4.74, 4.98 (2H, ABq, 17 Hz), 4.93 (2H, s), 5.55 (1H, d, 2 Hz), 6.60 (1H, d, 2 Hz), 7.73 (4H, d).

EXAMPLE 13

Tetrahydropyranylation of the Bromohydrin IV J

The bromohydrin IV J (56 mg, 0.12 mmol) was dissolved in methylene chloride (5 mL) and to this solution were added dihydropyran (0.5 mL) and anhydrous p-toluenesulfonic acid (2 mg). The mixture was stirred at room temperature for 50 min and was then poured onto ice-cold 5% sodium bicarbonate (30 mL). Extraction with chloroform (3×40 mL), followed by washing of the chloroform extracts with brine (2×20 mL), drying (Na$_2$SO$_4$) and evaporation yielded 79 mg of an oil. This was purified by plc (silica gel, 30% acetone in hexane, two developments) to give the tetrahydropyranyl ether IV K (36 mg, 55%). $^1$Hmr (CDCl$_3$, δ): 1.68 (6H, m), 3.73 (2H, m), 3.90 (3H, s) 4.40, 4.64 (2H, Abq, 14 Hz), 4.52 (1H, s), 4.72 (2H, s), 5.57 (1H, d, 2 Hz), 6.25 (1H, d, 2 Hz), 7.97 (4H, d).

EXAMPLE 14

Conversion of the Bromoformate IV H to the Acetoxyformate IV P

A solution of the bromoformate IV H (137 mg, 0.28 mmol) in methylene chloride (4.5 mL) was cooled to −15° C. and, under nitrogen, tetraethylammonium acetate (65 mg, 0.34 mmol) was added. The reaction mixture was stirred at −15° C. for 18 h and then at 0° C. for 24 h. It was then poured into ice-cold brine (20 mL), the layers were separated and the aqueous layer was extracted with methylene chloride (3×60 mL). The combined organic extracts were washed with brine (2×20 mL), dried (Na$_2$SO$_4$) and evaporated to 114 mg of a pale yellow foam. This was purified by plc (silica gel, acetone:hexane, 3:7) to give 79 mg (60%) of the acetoxyformate IV P. $^1$Hmr (CDCl$_3$, δ): 2.07 (3H, s), 3.87 (3H, s), 4.89, 5.12 (2H, ABq, 12 Hz), 5.13 (2H, s), 5.53 (1H, d, 2 Hz), 6.20 (1H, d, 2 Hz), 7.72 (4H, d), 7.97 (1H, s).

The acetoxyformate (79 mg, 0.172 mmol) was dissolved in methylene chloride (3 mL) and, at 0° C. under nitrogen, N methanolic hydrogen chloride (0.17 mL) was added. The solution was stored at 0° C. for 3 h and the solvent was then removed under reduced pressure. The residue was purified by plc (silica gel, acetone:hexane, 2:3, two developments) to give the acetoxylactone IX (R$_4$NH=Ft; R$_1$=OAc), 59 mg (90%). $^1$Hmr (CDCl$_3$, δ): 2.10 (3H, s), 4.87 (2H, s), 5.20 (2H, s), 5.55 (1H, d, 2 Hz), 6.58 (1H, d, 2 Hz), 7.70 (4H, br s).

EXAMPLE 15

Preparation of Chloroacetidinone A (R$_4$=TrOC; R$_3$=CH$_3$)

A solution of methyl 6-trichloroethoxycarbonylaminopenicillanate (68.4 g, 0.168 mmol) in methylene chloride (600 mL) was cooled to −78° C., and a precooled (−78° C.) solution of chlorine (23.9 g, 0.336 mmol) in methylene chloride (47 mL) was added dropwise, with stirring. Stirring was continued for 1 h at −78° C., and the reaction mixture was then brought to room temperature. Evaporation of the solvent under reduced pressure afforded a pale yellow foam, which crystallized upon trituration with ice-cold ether. The chloroazetidinone was collected, and washed with ice-cold ether: 48.7 g (70%), m.p. 139°-140° C. $^1$Hmr (CDCl$_3$, δ): 2.03 (3H, s), 2.30 (3H, s), 3.80 (3H, s), 4.77 (2H, s), 4.93 (1H, dd, 2, 8 Hz), 5.83 (1H, br s), 6.47 (1H, br d, 8 Hz).

EXAMPLE 16

Preparation of Dibromide V B

To a suspension of A (R$_4$=TrOC; R$_3$=CH$_3$) (49 g, 0.12 mmol), and carbon tetrachloride (450 mL), were added N-bromosuccinimide (47 g, 0.264 mmol) and benzoyl peroxide (0.5 g). The mixture was brought to rapid reflux, under nitrogen, and was then irradiated for 3 h over a Sylvania ® No. 2 Superflood ® lamp, cooled to room temperature, and filtered to remove succinimide. The filtrate was washed successively with ice-cold 5% sodium bisulfite (2×50 mL) and ice-cold brine (2×50 mL), and dried (MgSO$_4$). Evaporation afforded 72.2 g of V B (100%), as a pale yellow foam, which could be used directly in further reactions. $^1$Hmr (CDCl$_3$, δ): 3.90 (3H, s), 4.33 (2H, s), 4.53, 4.70 (2H, ABq, 10 Hz), 4.77 (2H, s), 4.90 (1H, dd, 2, 8 Hz), 6.00 (1H, d, 2 Hz), 6.53 (1H, d, 8 Hz).

EXAMPLE 17

Preparation of Diformate V A

A solution of V B (2.107 g, 3.72 mmol), in chloroform (20 mL), was cooled to 0° C. and, under nitrogen, treated dropwise during 5 min with a solution of tetramethylguanidinium formate (2.576 g, 16 mmol) in chloroform (8 mL). Stirring was continued for 30 min at 0° C. and then overnight at room temperature. The reaction mixture was poured onto ice-cold brine (20 mL), and the layers were separated. The aqueous layer was extracted with methylene chloride (3×40 mL). The combined organic layers were washed with brine (3×20 mL), dried (Na$_2$SO$_4$) and evaporated to give the crude product as a light brown foam. Purification on silica gel (10% acetone in hexane) afforded 483 mg (26%) of V A as a pale yellow foam. $^1$Hmr (CDCl$_3$, δ): 3.90 (3H, s), 4.77 (2H, s), 4.90 (1H, dd, 2, 8 Hz), 4.97 (2H, s), 5.17, 5.31 (2H, ABq, 12 Hz), 6.00 (1H, d, 2 Hz), 6.37 (1H, d, 8 Hz), 8.10 (2H, s). Anal. calcd. for C$_{14}$H$_{14}$N$_2$O$_9$Cl$_4$: C, 33.89; H, 2.84; N, 5.65. Found: C, 33.53; H, 2.82; N, 5.86.

EXAMPLE 18

Hydrolysis of Diformate V A

The diformate (250 mg, 0.5 mmol) was dissolved in methylene chloride (6 mL), the solution was cooled to 0° C., and methanolic hydrogen chloride (1 mL of a 2 M solution, 2 mmol) was added. The reaction mixture was stirred for 1 h at 0° C. by which time the starting material had disappeared. The solvent was removed under reduced pressure, and the product was taken up in methylene chloride (20 mL) and washed with cold brine (1×20 mL), dried (Na$_2$SO$_4$) and evaporated to give IX (R$_4$=TrOC; R$_1$=OH) as a white foam which appeared homogeneous by tlc, 202 mg (100%). $^1$Hmr (CD$_3$COCD$_3$, δ): 4.17 (1H, br s, exch D$_2$O), 4.71, 4.86 (2H, ABq, 18 Hz), 4.90 (2H, s), 5.10 (2H, s) 5.10 (1H, dd, 2, 8 Hz), 6.47 (1H, d, 2 Hz), 7.90 (1H, d, 8 Hz).

EXAMPLE 19

Conversion of V A to V H and V I

An ice-cold solution of V A (3.394 g, 6.84 mmol) in methylene chloride (40 mL) was treated dropwise, under nitrogen, with a solution of boron tribromide (1.025 g, 4.09 mmol) in methylene chloride (10 mL). The addition required 15 min, and stirring was continued at 0° C. for an additional 30 min. The solution was then poured onto ice-cold 2.5% potassium bicarbonate and, after shaking, the layers were separated. The aqueous layer was extracted with methylene chloride (3×50 mL) and the combined organic extracts were washed with brine (2×10 mL) and dried (Na$_2$SO$_4$). Evaporation left a pale yellow foam, 3.515 g, which was subjected to silica gel chromatography. Elution with 15% acetone-hexane yielded three fractions. The first was the dibromide V B (418 mg, 11%); the second was a mixture of V H and V I (2.217 g, 61%), and the third fraction was unreacted V A (315 mg, 9%).

EXAMPLE 20

Separation of V H and V I

The above mixture of geometrical isomers (2.2 g) was rechromatographed on silica gel using 20% ethyl acetate in hexane as eluant. This afforded pure V H (1.6 g) and V I (0.4 g). $^1$Hmr of V H (CDCl$_3$, δ): 3.88 (3H, s), 4.47, 4.61 (2H, ABq, 11 Hz), 4.75 (2H, s), 4.88 (1H, dd, 2, 7 Hz), 5.02 (2H, s), 5.95 (1H, d, 2 Hz), 6.34 (1H, d, 7 Hz), 8.05 (1H, s). Anal. calcd. for C$_{13}$H$_{13}$N$_2$O$_7$BrCl$_4$: C, 29.40; H, 2.46; N, 5.28. Found: C, 29.65; H, 2.54; N, 4.80.

$^1$Hmr of V I (CDCl$_3$, δ): 3.88 (3H, s), 4.19, 4.35 (2H, ABq, 10 Hz), 4.73 (2H, s), 4.98 (1H, dd, 2, 6 Hz), 5.32 (2H, s), 5.98 (1H, d, 2 Hz), 6.05 (1H, d, 6 Hz), 8.05 (1H, s).

EXAMPLE 21

Conversion of V H to the Acetoxyformate V Q

A solution of tetramethylguanidinium acetate (300 mg 1.73 mmol) in chloroform (5 mL) was cooled to 0° C. and, with stirring, treated all at once with a solution of the bromoformate V H, (265 mg, 0.5 mmol) in chloroform (3 mL). Stirring was continued for 1 h at 0° C. and then at room temperature for 5 h. The mixture was then poured onto ice-cold brine (50 mL), the layers were separated, and the aqueous layer washed with methylene chloride (3×40 mL). The combined organic extracts were washed with brine, dried (Na$_2$SO$_4$) and evaporated to a light brown foam (239 mg). Purification by plc (silica gel, ethyl acetate:hexane, 3:7) afforded recovered V H (40 mg) and the acetoxyformate V Q (57 mg, 25%) as a colourless foam. $^1$Hmr (CDCl$_3$, δ): 2.08 (3H, s), 3.88 (3H, s), 4.75 (2H, s), 4.88 (1H, dd, 2, 7 Hz), 4.93 (2H, s), 5.04, 5.17 (2H, ABq, 14 Hz), 5.97 (1H, d, 2 Hz), 6.27 (1H, d, 7 Hz), 8.08 (1H, s).

EXAMPLE 22

Hydrolysis of V Q to the Acetoxyhydrin V R

A solution of the acetoxyformate V Q (57 mg, 0.11 mmol) in methylene chloride (3 mL) was cooled to 0° C. and treated with 2 M methanolic hydrogen chloride (0.1 mL). The resulting solution was stirred for 1 h at 0° C. and was then evaporated to dryness to give a product which retained the methyl ester and acetate groups, but had lost the formate group. $^1$Hmr (CDCl$_3$, δ): 2.10 (3H, s), 3.63 (1H, br s, exch D$_2$O), 3.83 (3H, s), 4.70 (2H, s), 4.83 (2H, s), 5.15 (2H, s), 5.16 (1H, dd, 2, 6 Hz), 6.38 (1H, d, 2 Hz), 6.38 (1H, 6 Hz).

EXAMPLE 23

Conversion of V I to the Acetoxyformate V P

The bromoformate V I (217 mg, 0.41 mmol) was dissolved in chloroform (3 mL) and the solution was added to an ice-cold solution of tetrabutylammonium acetate (223 mg, 0.74 mmol) in chloroform (3 mL). The resulting solution was stirred at 0° C. for 3 h under nitrogen, and then at room temperature for 22 h. It was then poured onto ice-cold brine (30 mL), the layers were separated, and the aqueous layer was washed with methylene chloride (3×40 mL). The combined organic extracts were washed with brine (2×20 mL), dried (Na₂SO₄) and evaporated. The resulting material was purified by plc (silica gel, ethyl acetate:hexane, 3:7, three developments) to give 100 mg (48%) of the acetoxyformate V P. ¹Hmr (CDCl₃, δ): 2.10 (3H, s), 3.90 (3H, s), 4.80 (2H, s), 4.87 (2H, s), 4.97 (1H, dd, 2, 6 Hz), 5.23 (2H, s), 5.97 (1H, d, 2 Hz), 6.52 (1H, d, 6 Hz), 8.03 (1H, s).

EXAMPLE 24

Hydrolysis of V P to the Lactone IX ($R_4$=TrOC; $R_1$=OAc)

The acetoxyformate V P (100 mg, 0.20 mmol) was dissolved in methylene chloride (4 mL), the solution was cooled to 0° C., and methanolic hydrogen chloride (1 mL of a 0.8 M solution) was added. The resulting solution was stirred for 1.5 H, an additional 0.5 mL of M methanolic hydrogen chloride was added, and stirring was continued for 0.5 h. The reaction mixture was poured into cold 2.5% potassium bicarbonate (30 mL) and the layers were separated. The aqueous layer was extracted with methylene chloride (3×40 mL) and the combined organic extracts were washed with brine (2×20 mL) dried (Na₂SO₄) and evaporated to give the acetoxylactone as a colourless foam (74 mg, 83%), homogeneous by tlc. ¹Hmr (CDCl₃, δ): 2.13 (3H, s), 4.77 (2H, s), 4.90 (2H, s), 4.95 (1H, dd, 2, 6 Hz), 5.17 (2H, s), 6.38 (1H, d, 2 Hz), 6.57 (1H, d, 6 Hz).

EXAMPLE 25

Preparation of X

The bromoformate V H (133 mg, 0.25 mmol) was dissolved in dimethylformamide (6 mL), mercaptomethyltetrazole (35 mg, 0.30 mmol) was added, and the solution was stirred overnight at room temperature. The reaction mixture was then poured into ice-cold water (50 mL) and extracted with ethyl acetate (2×30 mL). This extract was washed successively with water (4×10 mL), saturated sodium bicarbonate (1×10 mL), and brine (1×10 mL), dried and evaporated to yield X as a colourless foam, homogeneous on tlc (125 mg, 91% yield); ¹Hmr (CDCl₃, δ): 3.88 (3H, s), 3.95 (3H, s), 4.39, 4.71 (2H, ABq, 14 Hz), 4.75 (2H, s), 4.93 (1H, dd, 2, 8 Hz), 4.98 (2H, br s), 5.95 (1H, d, 2 Hz), 6.67 (1H, d, 8 Hz), 8.03 (1H, s).

EXAMPLE 26

Preparation of XI(≡I) ($R_1$=OH,

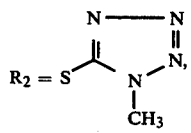

$R_3$=CH₃, R=H, $R_4$=TrOC)

Deformylation of X in the usual manner afforded XI(≡I). ¹Hmr (CDCl₃, δ): 3.45 (1H, br s, exch D₂O), 3.88 (3H, s), 3.98 (3H, s), 4.45 (2H, s), 4.62 (2H, s), 4.77 (2H, s), 4.90 (1H, dd, 2, 8 Hz), 6.02 (1H, d, 2 Hz), 6.95 (1H, d, 8 Hz).

EXAMPLE 27

Preparation of Diformate VI A

A slurry of 6-aminopenicillanic acid (21.6 g, 0.1 mmol), in water (250 mL), was cooled to 0°–5° C., and 2 N potassium hydroxide was added dropwise until a clear solution was obtained, and the pH was 7.5. This solution was diluted with tetrahydrofuran (200 mL). Then a solution of phenyl chloroformate (23.5 g, 19.1 mL, 0.15 mmol), in dry tetrahydrofuran (40 mL), was added dropwise, with stirring at 5°–10° C. and simultaneous addition of 2 N potassium hydroxide to maintain the pH in the range 7–8. The turbid reaction mixture was extracted with ethyl acetate (2×30 mL), and this extract was discarded. The aqueous layer was layered with ethyl acetate (300 mL), the system cooled to 5°–10° C. and, with stirring, the pH was adjusted to 1 with concentrated hydrochloric acid. The layers were separated, the aqueous layer extracted with ethyl acetate (3×150 mL), and the combined organic extracts were washed with saturated brine, dried (MgSO₄) and evaporated to yield phenoxycarbonylaminopenicillanic acid (31 g, 92%), as a crisp white foam; ¹Hmr (CDCl₃, δ): 1.60 (3H, s), 1.70 (3H, s), 4.47 (1H, s), 5.40–5.87 (2H, m), 6.00 (1H, br d, 10 Hz), 7.23 (5H, m). Methyl ester: ¹Hmr (CDCl₃, δ): 1.53 (3H, s), 1.67 (3H, s), 3.77 (3H, s), 4.45 (1H, s), 5.38–5.70 (2H, m), 6.12 (1H, br d, 10 Hz), 7.20 (5H, m).

To the methyl ester (7.973 g, 22.78 mmol), in methylene chloride (40 mL) at −78° C., was added, in one portion, a precooled solution of chlorine (3.234 g, 45.56 mmol) in methylene chloride (20 mL). The reaction mixture was stirred at −78° C. for 1 h, warmed to room temperature, and evaporated. Chromatography of the resulting foam (silica gel, 10%→30% ethyl acetate/hexane) gave pure A ($R_4$=PhOC; $R_3$=CH₃) (5.867 g, 73%) as a colourless foam. ¹Hmr (CDCl₃, δ): 2.00 (3H, s), 2.27 (3H, s), 3.73 (3H, s), 4.93 (1H, dd, 1.5, 8 Hz), 5.83 (1H, d, 1.5 Hz), 6.30 (1H, d, 8 Hz), 7.20 (5H, m). Anal. Calcd. for $C_{16}H_{17}N_2O_5Cl$: C, 54.47; H, 4.86; N, 7.94. Found: C, 54.18; H, 4.95; N, 7.62.

To a solution of A ($R_4$=PhOC; $R_3$=CH₃) (2.466 g, 7 mmol), in carbon tetrachloride (25 mL), were added N-bromosuccinimide (2.550 g, 14.2 mmol) and benzoyl peroxide (50 mg). Bromination was performed for 15 min, and the product isolated in the usual manner as a light brown foam (3.534 g). Chromatography on silica gel (ethyl acetate/hexane, 3/7) afforded pure VI B (2.446 g, 68%), as a colourless foam. ¹Hmr (CDCl₃, δ): 3.85 (3H, s), 4.30 (2H, s), 4.53, 4.72 (2H, ABq, 10.5 Hz), 4.87 (1H, dd, 1.5, 8 Hz), 6.03 (1H, d, 1.5 Hz), 6.10 (1H, d, 8 Hz), 7.22 (5H, m). The dibromide (3.060 g, 6 mmol) was dissolved in chloroform (25 mL), the solution was cooled to 0° C. and, under nitrogen, a solution of tetramethylguanidinium formate (4.0 g, 24.84 mmol), in chloroform (15 mL), was added dropwise during 5 min. The resulting solution was stirred at 0° and 30 min and then at room temperature for 15 h. It was then poured onto a mixture of ice and water and the layers were separated. The aqueous layer was washed with methylene chloride (3×40 mL), and the combined organic layers were washed with saturated brine (2×10 mL), dried (Na₂SO₄) and evaporated to a pale brown foam (2.30 g). The diformate VI A was isolated by chromatography on silica gel (10%→20% acetone-hexane); 689 mg (26%). ¹Hmr (CDCl₃, δ): 3.87 (3H, s), 4.88 (1H, dd, 1.8, 8 Hz), 4.97 (2H, s), 5.23 (2H, br s), 6.05 (1H, d, 1.8 Hz), 6.23 (1H, d, 8 Hz), 7.27 (5H, m), 8.10 (2H, s).

EXAMPLE 28

Hydrolysis of VI A

A solution of VI A (214 mg, 0.49 mmol), in methylene chloride (5 mL), was cooled to −10° C., and methanolic hydrogen chloride (2 mL, 29 mg/mL, 1.59 mmol) was added. The solution was allowed to stand overnight, by which time the starting material had disappeared and a single product had formed (tlc, silica gel, acetone:hexane, 3:1). The solvent was removed under reduced pressure and the residual light yellow foam was chromatographed on silica gel (30% acetone in hexane) to yield IX ($R_4$=PhOC; $R_1$=OH), 157 mg (91%) as a colourless foam. $^1$Hmr (CDCl$_3$, δ): 3.50 (1H, br s, exch D$_2$O), 4.38, 4.68 (2H, ABq, 16 Hz), 4.85 (2H, br s), 4.95 (1H, dd, 1.8, 8 Hz), 6.32 (1H, d, 1.8 Hz), 6.48 (1H, d, 8 Hz), 7.17 (5H, m).

EXAMPLE 29

Conversion of VI A to VI H and VI I

The diformate (184 mg, 0.42 mmol) was dissolved in methylene chloride (4 mL), and the solution was cooled to 0° C., under nitrogen. Then a solution of boron tribromide (61 mg, 0.24 mmol, 0157 mol-equiv) in methylene chloride (0.5 mL) was added dropwise during 5 min. The reaction mixture was stirred for 1 h at 0° C. and was then poured onto ice-cold 2.5% potassium bicarbonate (20 mL). The layers were separated, and the aqueous layer was extracted with methylene chloride (3×40 mL). The combined organic extracts were washed with saturated brine (2×20 mL), dried (Na$_2$SO$_4$), and evaporated to give the crude product (188 mg) as a yellow foam. This was purified by plc (silica gel, 40% acetone-hexane) to give three bands. The leading band (10 mg) was identified as the dibromide VI B, and the trailing band (30 mg) was unreacted diformate. The middle band, 102 mg (61%, based on recovered starting material) was the mixture of VI H and VI I, in the ratio of 4:1. $^1$Hmr of VI H (CDCl$_3$, δ): 3.77 (3H, s), 4.40, 4.57 (2H, ABq, 10 Hz), 4.78 (1H, dd, 2, 8 Hz), 4.92 (2H, s), 5.92 (1H, d, 2 Hz), 6.23 (1H, d, 8 Hz), 7.10 (5H, m), 7.90 (1H, s). $^1$Hmr of VI I (CDCl$_3$, δ): 3.67 (3H, s), 4.10, 4.27 (2H, ABq, 10 Hz), 4.78 (1H, dd, 2, 8 Hz), 5.23 (2H, s), 5.92 (1H, d, 2 Hz), 6.23 (1H, d, 8 Hz), 7.10 (5H, m), 7.90 (1H, s).

EXAMPLE 30

Removal of the 2,2,2-Trichloroethoxycarbonyl Protecting Group

A solution of naphthalene (727 mg, 5.68 mmol) in dry tetrahydrofuran (6 mL) was stirred at room temperature under nitrogen and treated with freshly cut sodium (129 mg, 1 equivalent). After 2 h, the dark green solution was treated with a solution of zinc chloride (382 mg, 2.8 mmol) in dry tetrahydrofuran (3.2 mL), to form a fine black precipitate. The mixture was centrifuged, and the solvent decanted. The residue was then washed by centrifugation with tetrahydrofuran (3×3 mL), and the residual black solid was dried under a stream of dry nitrogen. This solid was cooled to 0° C., mixed intimately with A ($R_4$=TrOC, $R_3$=CH$_3$) (40.8 mg, 0.1 mmol), and ice-cold 90% formic acid (3.6 mL) was added. The mixture was stirred vigorously at 0° for 5 min and then poured into cold saturated sodium bicarbonate (30 mL). The product was extracted into ethyl acetate (2×15 mL). The combined organic extracts were washed with saturated sodium bicarbonate (2×10 mL), saturated brine (10 mL), and dried over anhydrous sodium sulfate. Evaporation afforded a colourless solid (54.7 mg). This was triturated with cyclohexane (2×5 mL), to remove naphthalene, leaving a residue (24.7 mg, 106%). Analysis of this material by tlc (ethyl acetate) revealed naphthalene ($R_f$, 0.8) and the amine A ($R_4$=H, $R_3$=CH$_3$) ($R_f$, 0.3, yellow with ninhydrin). The infrared spectrum (CHCl$_3$) showed absorptions at 3450, 1775, 1720 cm$^{-1}$.

EXAMPLE 31 t-Butyldiphenylsilylation of the Hydroxylactone IX ($R_4$=TrOC, $R_1$=OH)

A solution of the hydroxylactone (40.8 mg), in purified dimethylformamide (0.25 mL), was treated, under nitrogen, with t-butyldiphenylchlorosilane (33 mg, 1.2 equivalents) and imidazole (17.0 mg, 2.5 equivalents), and then stirred at room temperature for 24 h. The reaction mixture was poured into water (5 mL) and the solution was extracted with ethyl acetate (2×5 mL). The combined organic extracts were washed successively with water (2×5 mL) and saturated brine (2.5 mL), dried over sodium sulfate and evaporated. The residual syrup was azeotroped with methylene chloride (2×6 mL) and then dried under high vacuum to a yellow foam (68.8 mg). This was purified by rapid chromatography on silica gel (5 g) (19:1 methylene chloride:ethyl acetate) to give, in addition to 20.7 mg of recovered hydroxylactone, 34.4 mg of compound IX ($R_4$=TrOC, $R_1$=O-t-butyldiphenylsilyl); IR (CHCl$_3$) 3443, 1790, 1755 cm$^{-1}$; $^1$Hmr (CDCl$_3$): 1.08 (9H, s), 4.82 (2H, s), 4.95 (2H, s), 5.08 (2H, br s), 5.08 (1H, dd, 2, 8 Hz), 5.95 (1H, br d, 8 Hz), 6.50 (1H, d, 2 Hz), 7.50–7.93 (10H, br m).

EXAMPLE 32

Conversion of IX ($R_4$=TrOC, $R_1$=O-t-butyldiphenylsilyl) to the Oxacephems 2A and 2B Activated zinc was prepared as described above, from naphthalene (218 mg), sodium (38.7 mg) and zinc chloride (114.6 mg). The silylated lactone (19 mg), in a mixture of acetonitrile (0.2 mL) and 90% formic acid (1.0 mL) was then added, and the mixture was stirred at 0° C. for 9 min. The product was isolated as described above: 13.3 mg, $^1$Hmr (CDCl$_3$): 1.07 (9H, s), 2.60 (2H, br s), 4.35 (1H, d, 2 Hz), 4.90 (4H, br m), 6.00 (1H, d, 2 Hz), 7.43 (10H, br m). This compound has structure IX ($R_4$=H, $R_1$=t-butyldiphenylsilyl).

The amine was dissolved in dry tetrahydrofuran (0.5 mL) and, under nitrogen, 50 microliters of a 1.0 M solution of tetrabutylammonium fluoride in tetrahydrofuran were added. The solution was maintained at room temperature for 20 min and then diluted with ethyl acetate (10 mL) and added to water (20 mL). The aqueous layer was extracted with ethyl acetate (10 mL), and the combined organic layers were washed with water (10 mL), saturated brine (10 mL), dried over sodium sulfate, and evaporated to afford the product, 9.3 mg, $R_f$(ethyl acetate): 0.26 (orange-brown with ninhydrin), IR(CHCl$_3$): 1818, 1750 cm$^{-1}$. This material has the structure

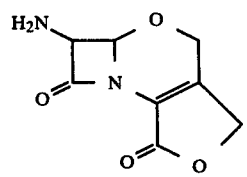

2A

Acylation of compound 2A with, for example, phenyl acetyl chloride, affords the oxacephem 2B

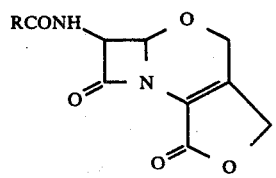

where R=PhCH$_2$.

EXAMPLE 33

Conversion of 1 (R=H, R$_1$=OH,

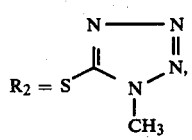

R$_3$=CH$_3$, R$_4$=TrOC) to the Oxacephem 3B

The product of Example 26 was silylated, as described in Example 31 and then cyclized with fluoride ions, as described in Example 32. The product was treated with activated zinc as described in Example 30 to give the oxacephem 3A, having the characteristic IR absorption at 1800 cm$^{-1}$.

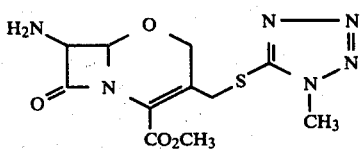

Acylation of oxacephem 3A with, for example, phenyl acetyl chloride, affords the oxacephem 3B (R=PhCH$_2$)

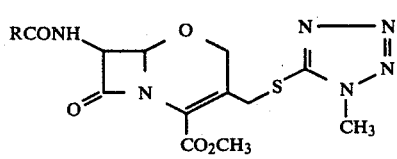

We claim:

1. A process for preparing a 1-oxacephem derivative of the formula I

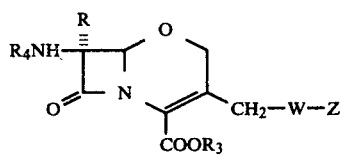

in which R$_4$ is hydrogen or a cleavable amino-protecting acyl group, or R$_4$NH represents phthalimido, R$_3$ is hydrogen or a cleavable carboxy-protecting group, R$^2$ is hydrogen or methoxy, W is NH, O, or S and Z is selected from lower acyl groups and from five membered heterocycles containing 1-4 hetero atoms and optionally substituted with loweralkyl, which comprises treating a compound of the formula II

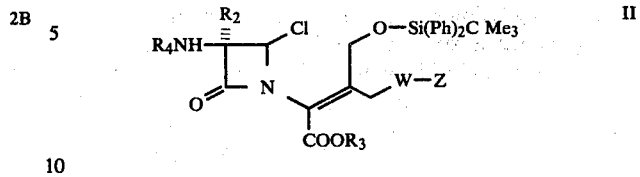

in which R$_4$, R$_3$, R$_2$, W and Z are as defined above with fluoride ions, and isolating the corresponding compound of formula I.

2. A process as claimed in claim 1 wherein the compound of formula II is prepared by treating a compound of the formula IIIa:

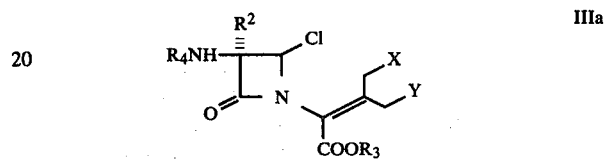

in which R$_4$, R$_2$, R$_3$, W and Z are as defined in claim 1 and R$_1$ is hydrogen with t-butyldiphenylsilyl chloride, and isolating the corresponding compound of formula II.

3. A process as claimed in claim 2 wherein the compound of formula IIIa is prepared by treating a compound of the formula IIIb

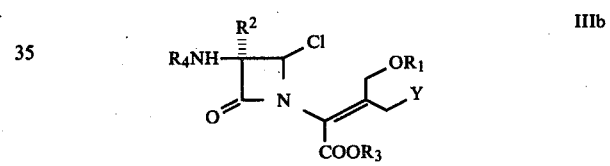

in which R$_4$, R$_3$ and R$_2$ are as defined in claim 2, R$_1$ is CHO, and Y is a halogen, with a compound of the formula HWZ in which W and Z are as defined in claim 2, and isolating the corresponding compound of formula IIIa in which R$_1$ is CHO; treating said last-named compound of formula IIIa with a hydrolyzing agent, and isolating the corresponding compound of formula IIIa in which R$_1$ is hydrogen.

4. A process as claimed in claim 3 in which the compound of formula IIIb in which R$_1$ is hydrogen is prepared by treating a compound of formula III

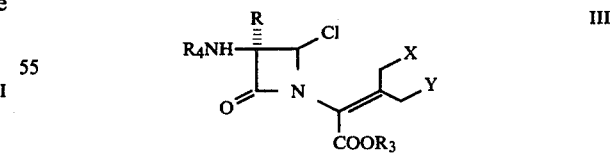

in which R$_4$, R$_3$, R$_2$ and Y are as defined above and X is the same halogen as Y (a) with a formylating agent in a halogenated hydrocarbon solvent to obtain the corresponding compound of formula III in which X and Y are both OCHO;

(b) treating said last-named compound with less than one molar equivalent of a boron halide, to obtain a 2:1 to 4:1 mixture of the corresponding compounds of formula III in which X is OCHO and Y is the corresponding halogen with the corresponding compound of formula III in which X is the corresponding halogen and Y is OCHO; separating said last-named mixture, and isolating the corresponding compound of formula III in which X is OCHO and Y is the corresponding halogen;

(c) treating said last-named compound of formula III in which X is OCHO and Y is the corresponding halogen with a hydrolyzing agent and isolating the corresponding compound of formula III in which X is OH and Y is the corresponding halogen;

(d) alternatively, treating the last-named compound of formula III of (b) with a tetraalkylammonium acetate or with a heterocyclic mercaptan of the general formula HSHET, where HET is a five or six membered aromatic heterocycle containing 1-4 heteroatoms and optionally substituted with lower alkyl, and isolating the corresponding product of formula III in which X is OCHO and Y is OAc or SHET prior to the hydrolysis step of (c).

5. A process as claimed in claim 4 wherein HET is selected from furyl, thienyl,

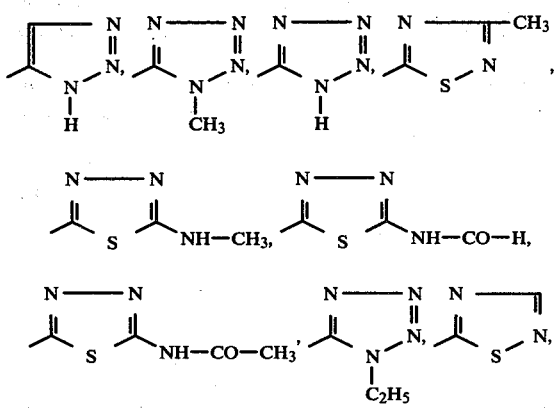

-continued

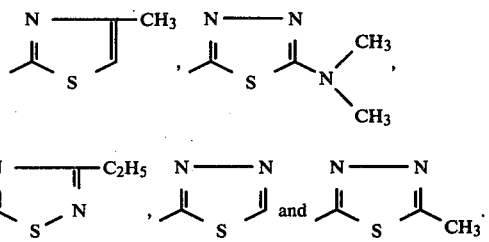

6. A process as claimed in claim 4 in which the formylating agent is selected from tetra(lower alkyl)-guanidinium formates and tetra(lower alkyl)ammonium formates.

7. A process as claimed in claim 4 in which the formylating agent is selected from tetramethylguanidinium formate and tetra-n-butylammonium formate.

8. A process as claimed in claim 4 in which the halogenated hydrocarbon solvent has 1-2 carbon atoms and 2-4 halogen atoms in which the halogen has an atomic weight greater than 19.

9. A process as claimed in claim 4 in which the halogenated hydrocarbon solvent is methylene (di)chloride.

10. A process as claimed in claim 4 in which the boron halide is used in quantities of 0.3 to 0.7 molar equivalents.

11. A process as claimed in claim 1 in which the hydrolyzing agent is a mineral acid dissolved in a lower alkanol.

12. A process as claimed in claim 4 in which the hydrolyzing agent is hydrochloric acid dissolved in methanol.

13. A process as claimed in claim 4 in which the treatment with the formylating agent is carried out at ambient temperature, the treatment with the boron halide is carried out within a temperature range of from $-10°$ C. to $2°$ C., and the hydrolysis is carried out with a temperature range of from $-5°$ C. to $5°$ C.

* * * * *